(12) United States Patent
Tiberi

(10) Patent No.: US 11,497,827 B2
(45) Date of Patent: Nov. 15, 2022

(54) FREE-STANDING ECOLOGICAL MULTI-PURPOSE DEVICE MADE OF A PLANT POLYMER, PREFERABLY MADE OF CARDBOARD, FOR THE PROGRESSIVE RELEASE OF SCENTS AND FRAGRANCES INTO THE ENVIRONMENT

(71) Applicant: Stefano Tiberi, Ardea (IT)

(72) Inventor: Stefano Tiberi, Ardea (IT)

( * ) Notice: Subject to any disclaimer, the term of this patent is extended or adjusted under 35 U.S.C. 154(b) by 278 days.

(21) Appl. No.: 16/766,409

(22) PCT Filed: Nov. 7, 2018

(86) PCT No.: PCT/IB2018/058735
§ 371 (c)(1),
(2) Date: May 22, 2020

(87) PCT Pub. No.: WO2019/102289
PCT Pub. Date: May 31, 2019

(65) Prior Publication Data
US 2020/0376151 A1    Dec. 3, 2020

(30) Foreign Application Priority Data
Nov. 24, 2017   (IT) .......................... 102017000135091

(51) Int. Cl.
*A61L 9/12*    (2006.01)
*A47K 10/16*    (2006.01)
(Continued)

(52) U.S. Cl.
CPC .............. *A61L 9/125* (2013.01); *A47K 10/16* (2013.01); *C08L 101/00* (2013.01); *A47K 2010/322* (2013.01)

(58) Field of Classification Search
CPC ... A61L 9/125; A47K 10/16; A47K 2010/322; C08L 101/00
(Continued)

(56) References Cited

U.S. PATENT DOCUMENTS

D347,470 S  *  5/1994  Kehrberger ................... D23/366
D365,390 S  *  12/1995  King ............................. D23/366
(Continued)

FOREIGN PATENT DOCUMENTS

AU           2007383 A      3/1985
GB           777303 A       6/1957
(Continued)

OTHER PUBLICATIONS

International Search Report, dated Feb. 19, 2019, from corresponding PCT application No. PCT/IB2018/058735.
(Continued)

*Primary Examiner* — Stephen M Gravini
(74) *Attorney, Agent, or Firm* — Nixon & Vanderhye

(57) ABSTRACT

A free-standing device for releasing fragrances includes a hollow external cylinder having an inner surface engaging the outer surface of an internal cylinder, the internal cylinder being closed. The inner surface of the external cylinder and the outer surface of the internal cylinder are fully at contact with each other. If open, the internal cylinder projects beneath the external cylinder, allowing the user to insert it into a support having a resting surface and an upper projection perforated centrally. The upper projection has aeration holes, sliding the internal cylinder with respect to the external cylinder exposing a portion of the inner surface of the external cylinder and the outer surface of the internal cylinder. A perfumed scent is applied on the inner surface of the external cylinder and/or on the outer surface of the
(Continued)

internal cylinder; the internal cylinder having break-lines for removing portions of the internal cylinder.

20 Claims, 1 Drawing Sheet

(51) Int. Cl.
*C08L 101/00* (2006.01)
*A47K 10/32* (2006.01)
(58) Field of Classification Search
USPC .......................................................... 239/34
See application file for complete search history.

(56) References Cited

U.S. PATENT DOCUMENTS

| | | | |
|---|---|---|---|
| 5,857,621 A * | 1/1999 | Poulos | A47K 10/22 239/57 |
| 6,575,383 B2 | 6/2003 | Dobler et al. | |
| 7,716,849 B1 * | 5/2010 | Hicks | D06F 59/04 34/106 |
| D617,439 S * | 6/2010 | Valentino | D23/367 |
| 7,942,388 B2 * | 5/2011 | Suissa | A61L 9/122 261/45 |
| 9,085,438 B2 * | 7/2015 | Wilkins | B65H 75/08 |
| 9,140,497 B2 * | 9/2015 | Al-Shahrani | F26B 25/18 |
| 10,330,384 B2 * | 6/2019 | Leung | F26B 21/006 |
| 10,500,566 B2 * | 12/2019 | Lesseraux | B01J 20/043 |
| 10,940,279 B2 * | 3/2021 | Keener | A61M 21/02 |
| 11,231,228 B2 * | 1/2022 | Palmer | F26B 9/003 |
| 2002/0066798 A1 * | 6/2002 | Laudamiel-Pellet | A61L 9/042 239/34 |
| 2003/0186643 A1 * | 10/2003 | Feuillard | B60H 3/0007 454/157 |
| 2004/0050950 A1 | 3/2004 | Brown | |
| 2005/0218243 A1 * | 10/2005 | Zobele | A01M 1/2033 239/34 |
| 2006/0196100 A1 * | 9/2006 | Laudamiel-Pellet | A61L 9/125 43/1 |
| 2010/0140372 A1 | 6/2010 | Patrick | |
| 2020/0376151 A1 * | 12/2020 | Tiberi | A47K 10/16 |

FOREIGN PATENT DOCUMENTS

| | | | |
|---|---|---|---|
| JP | 2002238988 A | 8/2002 | |
| JP | 2015198825 A | 11/2015 | |
| WO | WO-2019102289 A1 * | 5/2019 | ............ A47K 10/16 |

OTHER PUBLICATIONS

Written Opinion, dated Feb. 19, 2019, from corresponding PCT application No. PCT/IB2018/058735.
International Preliminary Report on Patentability, dated May 26, 2020 from corresponding PCT application No. PCT/IB2018/058735.

* cited by examiner

FREE-STANDING ECOLOGICAL MULTI-PURPOSE DEVICE MADE OF A PLANT POLYMER, PREFERABLY MADE OF CARDBOARD, FOR THE PROGRESSIVE RELEASE OF SCENTS AND FRAGRANCES INTO THE ENVIRONMENT

FIELD OF THE ART

The present invention regards the field of diffusers for releasing fragrances into the environment. More in detail, it regards a perfume diffuser for any domestic environment.

PRIOR ART

Various perfume diffusers for homes are already available in the market. Generally, these are plastic objects into which a refiller containing the desired perfume is inserted. Diffusion can occur continuously by connecting the device to an electrical socket, by means of an electrical resistor which, by heating the perfumed element, determines the diffusion of the fragrance in the surrounding environment. A second method for dispensing the perfume is through sprays which occur at predetermined time intervals or when a special sensor detects a person transiting near the diffuser.

Some of these devices are also object of international patents such as, for example, the Japanese patent No JP 2015 198 825. This patent has the object of claiming a compact and stable fragrance diffuser, so as to prevent it from falling and breaking.

All these devices are expensive and difficult to dispose.

Furthermore, they generate additional waste among domestic waste.

An object of the present invention is to describe a perfume diffuser that does not require any form of power supply and that is eco-friendly.

A second object of the diffuser described herein is to simplify the use of the fragrance diffusion devices, by providing a modular object in which the amount of perfume released can be easily adjusted by the user.

DESCRIPTION OF THE INVENTION

According to the present invention, a free-standing device that releases any perfumed fragrance in an adjustable manner is provided, thus effectively overcoming the problems outlined above.

Said device is entirely made of any plant polymer, preferably made cardboard, thus effectively solving ecological problems.

Advantageously, said device consisting of a first external cylindrical support and a second internal cylindrical support, coaxial and hollow, positioned in a first closed configuration in which the inner surface of the external cylindrical support and the outer surface of the internal cylindrical support are fully at contact with each other. At least one perfumed essence is applied, in any suitable manner, on said inner surface of said external cylindrical support and/or on said outer surface of said internal cylindrical support and, when the support is in a first closed configuration, the diffusion of the perfume is prevented. Said first closed configuration is characterised in that the surfaces at contact of the external cylindrical support and the internal cylindrical support cover each other.

A support consisting of a lower flat resting surface and an upper cylindrical projection is engaged beneath the internal cylindrical support. The latter is centrally provided with a hole into which the lower portion of the internal cylindrical support is inserted. More in detail, the upper cylindrical projection of the support embraces the outer surface of the lower portion of the internal cylindrical support.

In its portion for attachment to the resting surface, said upper cylindrical projection is provided with a plurality of aeration holes thanks to which the circulation of air around the device is improved and thus the diffusion of fragrance in the environment is improved. In the its preferred embodiment, the support consists of a flat surface provided with a plurality of grooves in proximity of the central hole. The latter confer to the central hole a given elasticity which allows perfect adherence between said support and the lower portion of the internal cylindrical support of the device.

Advantageously, said lower support surface of said support can be provided with velcro, with a magnet or with an adhesive layer which allow the application of the device even on vertical surfaces of various types.

Advantageously, by sliding said internal cylindrical support along the longitudinal axis, said device can take a second open configuration, characterised in that said internal cylindrical support projects at the lower part with respect to said external cylindrical support, freeing inside the device at least one surface portion suitable to release the perfumed essence. Advantageously, irrespective of the surface soaked with perfume, it can be divided into two differently perfumed sectors so that, by sliding the internal cylindrical support to one side, a given essence will be diffused and a different essence will be diffused by making it slide to the opposite side.

Advantageously, said internal cylindrical support is provided with a plurality of break-lines, suitable to remove, in a precise and predetermined fashion, the internal cylindrical support portion projecting into said second open configuration. Preferably, said break-lines will be perpendicular to the longitudinal axis of the internal cylindrical support, thus describing a plurality of circumferences preferably equally spaced.

In order to guarantee the static sealing between said internal cylindrical support and said external cylindrical support, especially when the device is advantageously in said second open configuration, the outer surface of the internal cylindrical support and/or the inner surface of the external cylindrical support, can be provided with at least one relief consisting of a thickening element of any shape, comprised between 0.5 mm and 3 mm, preferably 1 mm, projecting from the outer surface of the internal cylindrical support and/or the inner surface of the external cylindrical support.

Even the inner surface of the internal cylindrical support can be, similarly, provided with at least one relief, suitable to improve the grip that the user obtains on said internal cylindrical support to make it slide with respect to said external cylindrical support, taking the device from the closed configuration to the open configuration.

Advantageously, said device can be provided with a toilet paper or paper towel roll wound around the outer surface of the external cylindrical support. Alternatively, the size of the entire device can be suitably selected so that the entire device can be inserted into a common toilet paper or paper towel roll.

DESCRIPTION OF THE FIGURES

The invention will be described hereinafter in at least one preferred embodiment, provided by way of non-limiting illustration, with reference to the attached figures, wherein.

DETAILED DESCRIPTION OF THE INVENTION

Now, the present invention will be illustrated purely by way of non-limiting example, with reference to the figures illustrating some embodiments regarding the present inventive concept.

Figure 1:
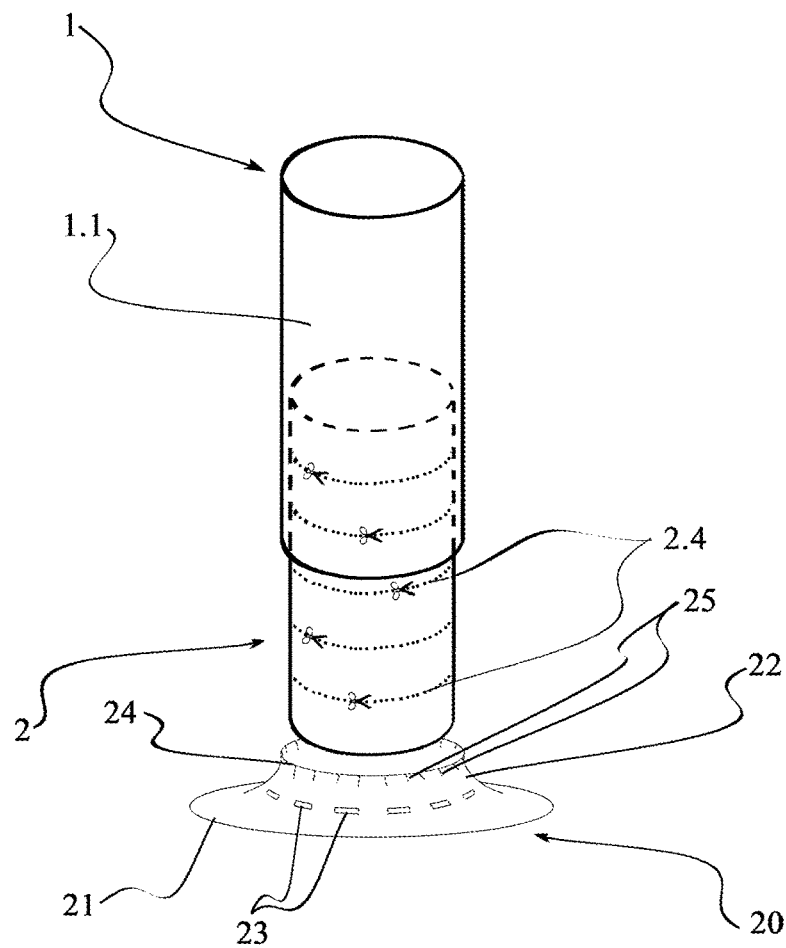
FIG. 1 shows a three-dimensional view of a device according to the present invention in which the external cylindrical support 1 and the internal cylindrical support 2 projecting beneath, can be seen. The break-lines 2.4, which describe, in this case, six equally spaced circumferences, highlighted by the scissors symbol, are shown thereon. The support 20 in all its components, i.e., the lower resting surface 21, the upper projection 22, the lateral holes 23 and the central hole 24 is illustrated at the lower part. In this case the upper projection 22 is provided with grooves 25.

With reference to FIG. 1, a fragrance diffuser consisting of the free-standing device of the present invention is shown.

The external cylindrical support 1 arranged coaxially to an internal cylindrical support 2 is shown. Due to the adherence between the inner surface 1.2 of the external cylindrical support 1 and the outer surface 2.1 of the internal cylindrical support 2, these two components can reversibly take, due to the action of a user, a first closed configuration and a second open configuration.

The first closed configuration is characterised in that the inner surface 1.2 of the external cylindrical support 1 and the outer surface 2.1 of the internal cylindrical support 2 are fully at contact with each other. The fact that these actually are the surfaces soaked with perfume entails that the diffusion of perfume in the environment is prevented in the first closed configuration.

In the second open configuration instead, the internal cylindrical support 2, sliding axially with respect to said external cylindrical support 1, projects at the lower part. The lower projecting portion is suitable to be inserted into the central hole 24 of a support 20 suitable to confer stability to the entire device.

In the second open configuration, a predetermined portion of the inner surface 1.2 of the external cylindrical support 1 and a similar portion of the outer surface 2.1 of the internal cylindrical support 2 are exposed, releasing the perfumed fragrance into the environment.

Said support 20 consists of a lower flat resting surface 21 and an upper cylindrical projection 22. While the lower flat resting surface 21 is suitable to allow the stable resting of the device on a horizontal surface or if provided with an adhesive, magnet or velcro also adhesion to a vertical or inclined surface, the upper cylindrical projection 22 is suitable to be engaged with the projecting portion of the internal cylindrical support 2.

Furthermore, said support 20 is provided with a plurality of lateral holes 23 suitable to facilitate the flow of air around and inside the device to increase the fragrance diffusion.

In the embodiment represented in FIG. 1, said support 20 consists of a flat surface provided with a plurality of grooves 25 in proximity of the central hole 24 which allow the projecting shape of the upper part of the support 20.

Furthermore, the internal cylindrical support 2 is also provided with a plurality of break-lines 2.4 suitable to allow the user to remove, in a precise and predetermined fashion, the internal cylindrical support portions 2 delimited by them. In this manner, the break-lines serve as a graduated scale for modulating the released dose of perfume preventing the open configuration from making the device too high.

Figure 2:
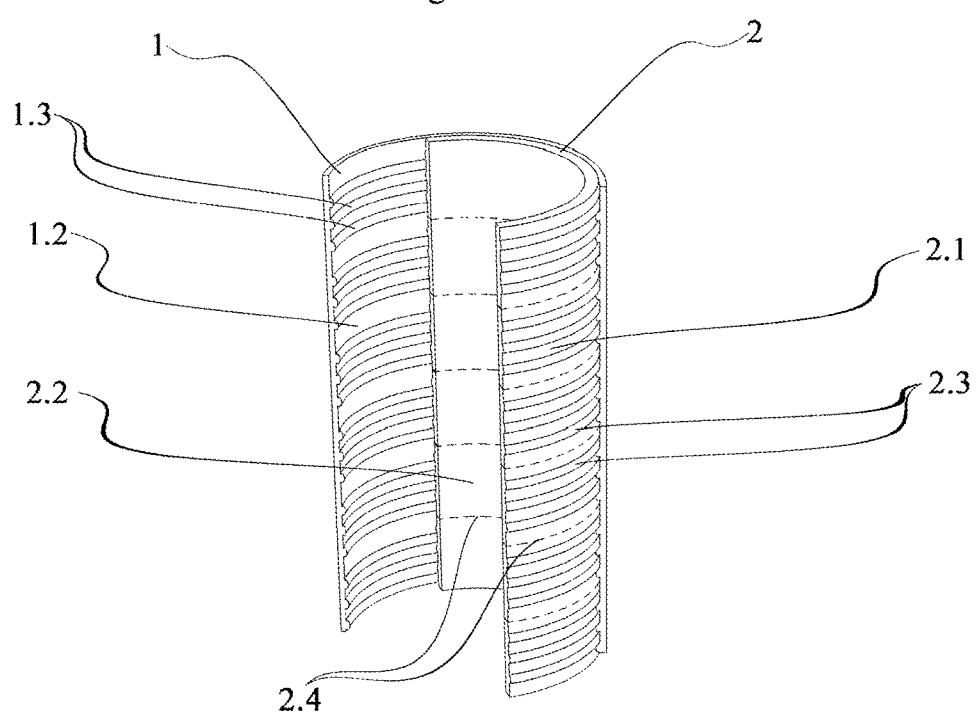
FIG. 2 shows a three-dimensional cross-section of a device showing the inner surface 1.2 provided with a plurality of reliefs 1.3 which end up engaged with the reliefs 2.3 present on the inner surface 2.1 of the internal cylindrical support 2; the circular break-lines 2.4 arranged on the internal cylindrical support 2 to allow the separate diffusion of the fragrance, are also shown.

With reference to FIG. 2 an embodiment of the device is shown, wherein the outer surface 2.1 of the internal cylindrical support 2 and the inner surface 1.2 of the external cylindrical support 1 are provided with reliefs 1.3-2.3 consisting of thickening elements comprised between 0.5 mm and 3 mm, preferably 1 mm, suitable to increase the static sealing of the device both in said closed configuration and in said open configuration.

All the components of the device are made of cardboard or any other plant polymer, thus making the device completely eco-friendly.

Lastly, it is clear that the invention described up to now may be subjected to modifications, additions or variants obvious to a man skilled in the art, without departing from the scope of protection outlined by the attached claims.

The invention claimed is:

1. A free-standing ecological multi-purpose device made of a plant polymer, for progressive release of fragrances and scents into an environment, the device comprising:
   a first hollow external cylindrical support, provided with an outer surface and an inner surface; and
   a second internal cylindrical support having an outer surface, the first hollow external cylindrical support being configured to be slidably reversibly engaged with the outer surface of the second internal cylindrical support of a same length, concentric and coaxial with respect to said external cylindrical support and internally hollow, said second internal cylindrical support being arranged in a first closed configuration, the inner surface of the first hollow external cylindrical support and the outer surface of the second internal cylindrical support being fully at contact with each other, said second internal cylindrical support being configured to take a second open configuration; and
   a base support,
   wherein said second internal cylindrical support, sliding axially with respect to said first hollow external cylindrical support, projects beneath with respect to said first hollow external cylindrical support to enable a user to insert the second internal cylindrical support into the base support that includes a lower flat resting surface and an upper cylindrical projection centrally provided with a central hole and configured to be engaged with the lower portion of the second internal cylindrical support, said upper cylindrical projection being provided with a plurality of aeration holes, sliding of the second internal cylindrical support with respect to the first hollow external cylindrical support, exposing a predetermined portion of the inner surface of said first hollow external cylindrical support and a similar outer surface portion of said second internal cylindrical support,
   wherein a predetermined amount of at least one common scent being applied, in any manner, on one or more of: (i) the inner surface of the first hollow external cylindrical support and (ii) the outer surface of the second internal cylindrical support, said inner surface of the first hollow external cylindrical support and the outer surface of the second internal cylindrical being configured to release a predetermined and controlled amount of the scent into the environment when said second internal cylindrical support is in said open configuration, said second internal cylindrical support being provided with a plurality of break-lines, equally spaced from each other, configured to enable the user to remove, in an accurate and predetermined manner, the portions of the second internal cylindrical support delimiting said break-lines to be able to spread the scent in the environment in a controlled manner, when said free-standing device is placed vertically on a flat surface, said break-lines being configured to serve as a gradual scale to regulate the amount of scent released into the environment.

2. The free-standing ecological multi-purpose device made of the plant polymer, for progressive release of the fragrances and the scents, according to claim 1, wherein the lower flat resting surface is provided with one of: (i) an adhesive layer, (ii) a magnetic element, and (iii) Velcro™ configured to enable stable application thereof on one of vertical, horizontal, and oblique planes.

3. The free-standing ecological multi-purpose device made of the plant polymer, for progressive release of the fragrances and the scents, according to claim 1, wherein one or more of the outer surface and the inner surface of the second internal cylindrical support is provided with at least one relief including a thickening element comprised between 0.5 mm and 3 mm projecting from one or more of the outer surface and the inner surface of the second internal cylindrical support, the thickening element being configured to increase static sealing of the device in said first closed configuration and said second open configuration.

4. The free-standing ecological multi-purpose device made of the plant polymer, for progressive release of the fragrances and the scents, according to claim 1, wherein the inner surface of the first hollow external cylindrical support is provided with at least one relief including a thickening element comprised between 0.5 mm and 3 mm, the thickening element being configured to increase static sealing of the device in said first closed configuration and said second open configuration.

5. The free-standing ecological multi-purpose device made of the plant polymer, for progressive release of the fragrances and the scents, according to claim 1, wherein, on one or more of the inner surface of the first hollow external cylindrical support and the outer surface of the second internal cylindrical support, two different scents are applied in any appropriate manner, each of the two different scents being disposed at one or more of: (i) one of two ends of the inner surface of the first hollow external cylindrical support and (ii) one of two ends of the outer surface of the second internal cylindrical support.

6. The free-standing ecological multi-purpose device made of the plant polymer, for progressive release of the fragrances and the scents, according to claim 1, wherein one or more of: (i) said first hollow external cylindrical support, and (ii) said second internal cylindrical support and said base support, are processed through a treatment configured to make the one or more of: (i) the first hollow external cylindrical support, and (ii) the second internal cylindrical support and said base support waterproof.

7. The free-standing ecological multi-purpose device made of the plant polymer, for progressive release of the fragrances and the scents, according to claim 1, wherein the lower flat surface of said base support is provided with a plurality of engravings in proximity of the central hole.

8. The free-standing ecological multi-purpose device made of the plant polymer, for progressive release of the fragrances and the scents, according to claim 1, wherein said first hollow external cylindrical support is configured to be inserted into a cylindrical support of a common toilet paper or paper towel roll.

9. The free-standing ecological multi-purpose device made of the plant polymer, for progressive release of the fragrances and the scents, according to claim 1, wherein a common toilet paper or paper towel is wound around said outer surface of said first hollow external cylindrical support.

10. The free-standing ecological multi-purpose device made of the plant polymer, for progressive release of the fragrances and the scents, of claim 1, wherein the device is made of cardboard.

11. The free-standing ecological multi-purpose device made of the plant polymer, for progressive release of the fragrances and the scents, according to claim 3, wherein the thickening element projects 1 mm from one or more of: (i) the outer surface of the second internal cylindrical support, and (ii) the inner surface of the second internal cylindrical support.

12. The free-standing ecological multi-purpose device made of the plant polymer, for progressive release of the fragrances and the scents, according to claim 2, wherein one or more of the outer surface and the inner surface of the second internal cylindrical support is provided with at least one relief including a thickening element comprised between 0.5 mm and 3 mm projecting from one or more of the outer surface and the inner surface of the second internal cylindrical support, the thickening element being configured to increase static sealing of the device in said first closed configuration and said second open configuration.

13. The free-standing ecological multi-purpose device made of the plant polymer, for progressive release of the fragrances and the scents, according to claim 4, wherein the thickening element is 1 mm.

14. The free-standing ecological multi-purpose device made of the plant polymer, for progressive release of the fragrances and the scents, according to claim 2, wherein the inner surface of the first hollow external cylindrical support is provided with at least one relief including a thickening element comprised between 0.5 mm and 3 mm, the thickening element being configured to increase static sealing of the device in said first closed configuration and said second open configuration.

15. The free-standing ecological multi-purpose device made of the plant polymer, for progressive release of the fragrances and the scents, according to claim 3, wherein the inner surface of the first hollow external cylindrical support is provided with at least one relief including a thickening element comprised between 0.5 mm and 3 mm, the thickening element being configured to increase static sealing of the device in said first closed configuration and said second open configuration.

16. The free-standing ecological multi-purpose device made of the plant polymer, for progressive release of the fragrances and the scents, according to claim 2, wherein, on one or more of the inner surface of the first hollow external cylindrical support and the outer surface of the second internal cylindrical support, two different scents are applied in any appropriate manner, each of the two different scents being disposed at one or more of: (i) one of two ends of the inner surface of the first hollow external cylindrical support and (ii) one of two ends of the outer surface of the second internal cylindrical support.

17. The free-standing ecological multi-purpose device made of the plant polymer, for progressive release of the fragrances and the scents, according to claim 3, wherein, on one or more of the inner surface of the first hollow external cylindrical support and the outer surface of the second internal cylindrical support, two different scents are applied in any appropriate manner, each of the two different scents being disposed at one or more of: (i) one of two ends of the inner surface of the first hollow external cylindrical support and (ii) one of two ends of the outer surface of the second internal cylindrical support.

18. The free-standing ecological multi-purpose device made of the plant polymer, for progressive release of the fragrances and the scents, according to claim 4, wherein, on one or more of the inner surface of the first hollow external cylindrical support and the outer surface of the second internal cylindrical support, two different scents are applied in any appropriate manner, each of the two different scents being disposed at one or more of: (i) one of two ends of the inner surface of the first hollow external cylindrical support and (ii) one of two ends of the outer surface of the second internal cylindrical support.

19. The free-standing ecological multi-purpose device made of the plant polymer, for progressive release of the fragrances and the scents, according to claim 2, wherein one or more of: (i) said first hollow external cylindrical support, and (ii) said second internal cylindrical support and said base support, are processed through a treatment configured to make the one or more of: (i) the first hollow external cylindrical support, and (ii) the second internal cylindrical support and said base support waterproof.

20. The free-standing ecological multi-purpose device made of the plant polymer, for progressive release of the fragrances and the scents, according to claim 3, wherein one or more of: (i) said first hollow external cylindrical support, and (ii) said second internal cylindrical support and said base support, are processed through a treatment configured to make the one or more of: (i) the first hollow external cylindrical support, and (ii) the second internal cylindrical support and said base support waterproof.

\* \* \* \* \*